United States Patent [19]

Tsaklakidis et al.

[11] Patent Number: 5,538,957
[45] Date of Patent: Jul. 23, 1996

[54] PHOSPHONOSUCCINIC ACID DERIVATIVES, PROCESSES FOR THEIR PREPARATION AND MEDICAMENTS CONTAINING THESE COMPOUNDS

[75] Inventors: Christos Tsaklakidis; Elmar Bosies, both of Weinheim; Angelika Esswein, Singen; Frieder Bauss, Lambsheim, all of Germany

[73] Assignee: Boehringer Mannheim GmbH, Mannheim, Germany

[21] Appl. No.: 244,245

[22] PCT Filed: Dec. 14, 1992

[86] PCT No.: PCT/EP92/02890

§ 371 Date: Jun. 3, 1994

§ 102(e) Date: Jun. 3, 1994

[87] PCT Pub. No.: WO93/12122

PCT Pub. Date: Jun. 24, 1993

[30] Foreign Application Priority Data

Dec. 19, 1991 [DE] Germany .................. 41 41 928.6

[51] Int. Cl.⁶ ...................... A61K 31/66; C07C 229/24
[52] U.S. Cl. .................. 514/114; 514/75; 514/553; 558/87; 558/141; 558/169; 560/11
[58] Field of Search ............... 514/75, 114, 553; 558/87, 141, 169; 562/11

[56] References Cited

U.S. PATENT DOCUMENTS 3,962,433  6/1976  Worms et al. .................. 558/87

OTHER PUBLICATIONS

CA97:216314, 1982.

*Primary Examiner*—Yogendra N. Gupta
*Attorney, Agent, or Firm*—Nikaido, Marmelstein, Murray & Oram

[57] ABSTRACT

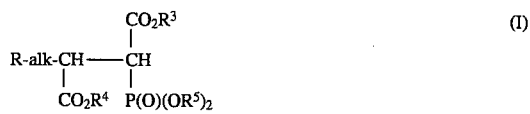

Compounds of the formula (I) in which: R is a possibly substituted amino group of the general form $-NR_1R_2$, in which $R_1$ and $R_2$ are independently hydrogen, lower alkyl, lower alkenyl or lower alkinyl, or R is a saturated, unsaturated or aromatic heterocyclic ring which may be mono or bi-substituted by lower alkyl or halogen; alk is a valency bond, a methylene, a saturated or unsaturated, straight or branched-chain alkylene chain with 2-6 carbon atoms; and $R^3$, $R^4$, $R^5$ are independently hydrogen, lower alkyl or benzyl; and their pharmacologically acceptable salts and enantiomers where, if $R^3=R^4=R^5=CH_3$ and alk is a valency bond, R may not be the dimethyl amino group. Process for their production and medicaments containing these compounds, for the treatment of calcium metabolic complaints.

5 Claims, No Drawings

PHOSPHONOSUCCINIC ACID DERIVATIVES, PROCESSES FOR THEIR PREPARATION AND MEDICAMENTS CONTAINING THESE COMPOUNDS

The present invention concerns new phosphonosuccinic acid derivatives, processes for their operation, as well as medicaments which contain these substances.

In Phosphorus and Sulphur 13, 85 (1982) is described the synthesis of 3-dimethylamino-2-dimethylphosphonosuccinic acid dimethyl ester but a pharmacological action of this compound is not known.

It has now been found that analogous phosphonosuccinic acid derivatives display an excellent action on the calcium metabolism and thus are suitable for the broad treatment of calcium metabolism disturbances. In particular, they can be very well used there where the bone build up and breakdown is disturbed, i.e. they are suitable for the treatment of diseases of the skeletal system, such as e.g. osteoporosis, Paget's disease, Bechterev's disease and the like.

However, on the basis of these properties, they can also find use for the therapy of urolithiasis and for the prevention of heterotopic ossifications. Furthermore, due to their influencing of the calcium metabolism, they also form a basis for the treatment of rheumatoid arthritis, of osteoarthritis and of degenerative arthrosis.

The subject of the present invention are compounds of the general formula I,

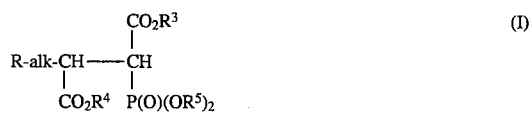

in which R signifies a possibly substituted amino group of the general formula $-NR^1R^2$, whereby, independently of one another, $R^1$ and $R^2$ each signify hydrogen, lower alkyl, lower alkenyl or lower alkynyl or R represents a saturated, unsaturated or aromatic heterocyclic ring which can possibly be substituted once or twice by lower alkyl or halogen, alk signifies a valency bond, a methylene, a saturated or unsaturated, straight-chained or branched alkylene chain with 2–6 carbon atom and $R^3$, $R^4$, $R^5$, in each case independently of one another, signify hydrogen, lower alkyl or benzyl, as well as their pharmacologically acceptably salts, whereby, for the case that $R^3=R^4=R^5=CH_3$ and alk signifies a valency bond, R cannot be the dimethylamino group.

In all cases, lower alkyl is to represent a straight-chained or branched $_1-C_6$-alkyl group, such as e.g. methyl, ethyl, propyl, isopropyl, butyl, isobutyl, pentyl or hexyl radical, especially methyl, ethyl, propyl, isobutyl or pentyl.

Lower alkenyl signifies unsaturated radicals with 3–6 carbon atoms, such as e.g. allyl, but 2-enyl, hexa-2,4-dienyl, above all allyl.

Lower alkynyl is to represent unsaturated radicals with 3–6 carbon atoms, such as e.g. propargyl, but- 3-ynyl, hex-5-ynyl but especially propargyl.

If the radical R signifies a saturated heterocyclic ring, it is a question of 3–8 membered rings which can also contain one or two further heteroactoms, such as the aziridine, azetidine, pyrrolidine, piperidine, azepine, morpholine or the thiomorpholine ring, especially the pyrrolidine, azepine and the morpholine ring.

If R signifies an unsaturated heterocyclic ring, as a rule it is a question of the imidazoline ring.

If R represents a hetero-aromatic ring, it is a question of a five- or six-membered ring, such as the pyridine, pyrimidine, pyrazine, imidazole, especially the pyridine and imidazole ring.

The heterocyclic rings can possibly by substituted once or twice by $C_1-C_6$-alkyl groups, preferably the methyl, ethyl or isopropyl group, as well as by chlorine or bromine.

In the case of the saturated or unsaturated, straight-chained or branched alkylene chains, alk represents radicals such as e.g. methylene, ethylene, propylene, butylene, 2-methylpropylene, pentylene, 1,1-dimethylpropylene, 2,3-dimethylpropylene, 2,2-dimethylpropylene, 2-methylbutylene, hexylene, 2,3-dimethylbutylene, 2-methylpentylene, 2-butenylene, 2-butynylene, especially methylene, ethylene, propylene, butylene, 2-methylpropylene, pentylene, hexylene and 2-butenylene.

Compounds of general formula I contain at least two assymmetric carbon atoms, therefore optically-active compounds of the general formula I are also the subject of the present invention.

Compounds of general formula I are prepared according to per se known processes, preferably in that one a) reacts carboxylic acid derivatives of the general formula II

in which R, alk and $R^4$ have the above-given meanings and Y signifies a group which can be removed, such as e.g. Hal or $O-SO_2-Z$, whereby Hal is to be chloride, bromide or iodide and Z methyl, phenyl, p-methylphenyl or p-nitrophenyl, with a phosphonoacetic acid ester of the general formula III

in which $R^3$ and $R^5$ possess the above-given meanings, whereby, for the case that R signifies a primary or secondary amino group, this must be present in protected form, perhaps as acylamino or phthaloylimido group, and possibly saponifies the resultant ester partly or completely to the corresponding acids of the general formula I, or b) reacts compounds of the general formula IV

in which R, alk, $R^3$ and $R^4$ have the above-given meanings, with a dialkyl phosphite of the general formula V

in which $R^5$ has the above-given meanings, and possibly saponifies the resultant ester partly or completely to the corresponding acids of the general formula I, or c) brings a compound of the general formula VI or VII

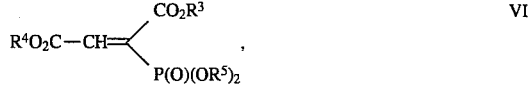

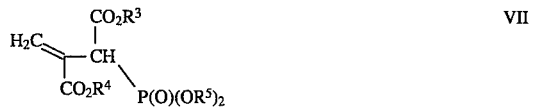

in which $R^3$, $R^4$ and $R^5$ possess the above-given meanings, to reaction is per se known manner with a compound of the general formula VIII

in which R possesses the above-given meanings and M signifies hydrogen or an alkali metal or alkaline earth metal, and possibly saponifies the resultant ester partly or completely to the corresponding acids of the general formula I and, if desired, converts into pharmacologically acceptably salts.

Compounds of the general formula II are so prepared that, for the case that Y=Hal, one halogenates a compound of the general formula IX

$$\text{R-alk}-\text{CH}_2-\text{CO}_2\text{R}^4 \quad \text{(IX)}$$

in which R, alk and $R^4$ possess the above-given meanings, according to processes known from the literature or, for the case that Y in formula II signifies the $O-SO_2-Z$ group, converts the hydroxyl group of a compound of general formula (X)

$$\text{R}-\text{alk}-\underset{\underset{\text{OH}}{|}}{\text{CH}}-\text{CO}_2\text{R}^4 \quad \text{(X)}$$

in which R, alk and $R^4$ possess the above-given meanings, into the corresponding sulphonic acid ester.

Some of the compounds of the general formula III are commercially available (Aldrich-Chemie GmbH & Co, KG) and, in special cases, are prepared by reaction of a haloacetic acid derivative of the general formula XI

$$\text{Hal}-\text{CH}_2-\text{CO}_2\text{R}^3 \quad \text{(XI)}$$

in which Hal and $R^3$ possess the above-given meanings, with a triphosphite of the general formula XII

$$\text{P(OR}^5)_3 \quad \text{(XII)}$$

in which $R^5$ possesses the above-given meaning.

Compounds of the general formula IV are prepared in that one
1. alkylates a compound of the general formula XIII

$$\text{R}-\text{H} \quad \text{(XIII)}$$

in which R possesses the above-given meaning, with a compound of the general formula XIV

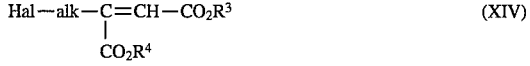
$$\text{Hal}-\text{alk}-\underset{\underset{\text{CO}_2\text{R}^4}{|}}{\text{C}}=\text{CH}-\text{CO}_2\text{R}^3 \quad \text{(XIV)}$$

in which Hal, alk, $R^3$ and $R^4$ possess the above-given meanings, or
2. dehydrates according to known processes a compound of the general formula XV

$$\text{R}-\text{alk}-\underset{\underset{\text{CO}_2\text{R}^4}{|}}{\text{CH}}-\underset{\underset{}{|}}{\overset{\overset{\text{OH}}{|}}{\text{CH}}}-\text{CO}_2\text{R}^3 \quad \text{(XV)}$$

in which R, alk, $R^3$ and $R^4$ possess the above-given meanings.

Compounds of general formula C are commercially available (Aldrich Co.).

Compounds of general formula VI are prepared in that one brings to reaction a compound of general formula V with an acetylene-dicarboxylic acid ester of the general formula XVI

$$\text{R}^4\text{O}_2\text{C}-\text{C}-\text{C}-\text{CO}_2\text{R}^3 \quad \text{(XVI)}$$

in which $R^3$ and $R^4$ have the above-given meaning.

Compounds of general formula VII are prepared in per se known manner in that one reacts a compound of the general formula XVII,

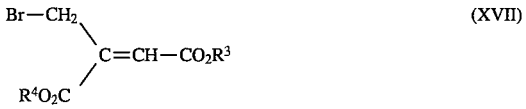

in which $R^3$ and $R^4$ possess the above-given meanings, with a compound of the general formula XII.

For the case that M does not signify hydrogen, compounds of the general formula VIII are metallised by processes according to the literature.

Compounds of the general formula IX are obtained according to known processes by alkylation of a compound of the general formula XIII with a compound of the general formula XVIII

$$\text{Hal}-\text{alk}-\text{CH}-_2-\text{CO}_2\text{R}^4 \quad \text{(XVIII)}$$

in which Hal, alk and $R^4$ possess the above-given meanings.

Compounds of the general formula X can be obtained by processes known from the literature by oxidation of the corresponding compounds of the general formula IX.

Compounds of the general formula XIV can be prepared in per se known manner in that one reacts a compound of the general formula XIX

in which $R^3$ and $R^4$ possess the above-given meanings, with a compound of the general formula XX

$$\text{Hal}-\text{alk}-\text{Hal} \quad \text{(XX)}$$

in which Hal and alk have the above-given meanings.

Compounds of the general formula XV are prepared in per se known manner by reaction of a compound of the general formula IX with a compound of the general formula XXI

in which $R^3$ possesses the above-given meanings.

One obtains compounds of the general formula XVII according to known methods by allylic bromination of a compound of the general formula XXII

in which $R^3$ and $R^4$ possess the above-given meanings.

The halogenation of a compound of the general formula IX takes place by its reaction with molecular halogen (chlorine, bromine, iodine), preferably bromine, without solvent or in an inert solvent, such as methylene chloride, chloroform or carbon tetrachloride, preferably carbon tetrachloride, and with addition of red phosphorus, phosphorus trichloride or phosphorus tribromide and at a temperature between room temperature and 100° C., preferably at 90° C. (K. Stoh, Chem. Pharm. Bull., 34, 2078 (1986); H. J. Ziegler, Synthesis, 1969, 39). Furthermore, compounds of the general formula IX can be halogenated in that metallises them in an aprotic solvent, such as tetrahydrofuran, and at low temperature, preferably at −78° C., with a lithium amide, such as lithium diisopropylamide, and subsequently reacts the compounds metallised in that -position of the general formula IX with bromine, iodine, carbon tetrachloride or carbon tetrabromide (M. Hesse, Helv. Chim, Acts 72, 847 (1989); R. T. Arnold, J. Org. Chem. 43, 2687 (1978) or with N-chloro- or N-bromosuccinimide (W. Oppolzer, Tetrahedron Lett. 26, 5037 (1985)).

The conversion of the hydroxyl group of a compound of the general formula X into a sulphonic acid ester group takes place according to conventional processes, such as e.g. by the condensation with a sulphonic acid chloride, such as methane-, benzene-, p-toluene- or p-nitrobenzenesulphonic acid chloride, in an inert solvent, such as methylene chloride, tetrahydrofuran or diethyl ether, preferably methylene chloride, with the use of an adjuvant base, such as trimethyl- or triethylamine or pyridien, preferably triethylamine, and at a temperature between 0° C. and room temperature.

For the preparation of compounds of the general formula XIX, see R. Eyjolfsson, Acta. Chem. Scand., 3075 (1970).

The reaction of a compound of the general formula II with a compound of the general formula III takes place, as a rule, in an aprotic solvent, such as toluene, tetrahydrofuran, diethyl ether or dimethylformamide, preferably dimethylformamide or tetrahydrofuran, with the use of a strong base, such as potassium hydride, sodium hydride, lithium diisopropylamide or lithium hexaneethyl disilylamide, preferably sodium hydride or lithium diisopropylamide, and at temperatures between −78° C. and 90° C. but preferably between −10° C. and room temperature.

The reaction of a compound of the general formula IV with a compound of the general formula V takes place under the conditions of the Michael addition in a solvent, such as methanol, ethanol, toluene, tetrahydrofuran, diethyl ether or dimethylformamide, preferably methanol, tetrahydrofuran or dimethylformamide, without further additions or with use of a base, such as sodium or potassium methylate or ethylate, sodium hydride, potassium hydride or lithium diisopropylamide, preferably sodium methylate, sodium hydride or lithium diisopropylamide, and at temperatures between −78° C. and 90° C. and preferably between −10° C. and room temperature.

As a rule, one carries out the reaction between a compound of the general formula VI or VII with a compound of the general formula VIII under the conditions of the Michael addition in a solvent, such as methanol, ethanol, toluene, tetrahydrofuran, diethyl ether or dimethylformamide, preferably methanol, tetrahydrofuran or dimethylformamide, without further additives or with use of a base, such as sodium hydride, potassium hydride, lithium diisopropylamide, butyl lithium, ethyl magnesium bromide, and possibly copper slat, such as copper chloride or bromide, for the formation of the corresponding cuprate of a compound of the general formula VIII (cf. G. H. Posner, Tetrahedron Letters, 37, 3215 (1977)) and at temperatures between −78° C. and 90° C., preferably between −78° C. and room temperature.

The reaction between a compound of the general formula XI with a compound of the general formula XII takes place, as a rule, without solvent at temperatures between room temperature and 150° C. preferably at 130° C. with a reaction time between 30 min and 30 hours, preferably 18 hours.

As a rule, one carries out the alkylation of a compound of the general formula XIII with a compound of the general formula XIV or of a compound of the general formula XVIII in a solvent, such as methanol, ethanol, propanol, tetrahydrofuran, diethyl ether or dimethylformamide, preferably methanol, tetrahydrofuran or dimethylformamide, with adjuvant bases or with addition of a base, such as potassium carbonate, sodium methylate, sodium or potassium hydride, lithium diisopropylamide, butyl lithium or phenyl lithium, preferably sodium hydride, potassium carbonate, butyl lithium or phenyl lithium, and at a temperature between −78° C. and the reflux temperature of the solvent used, preferably between −78° C. and 50° C. The dehydration of a compound of the general formula XV usually takes place in a solvent, such as benzen, toluene, xylene, chloroform or methylene chloride, preferably toluene or methylene chloride, with addition of dehydration agent, such as sulphuric acid, phosphoric acid, p-toluenesulphonic acid, preferably p-toluenesulphonic acid, and at a temperature between room temperature and reflux temperature of the solvent used, preferably at 100° C. for the reaction of a compound V with a compound XVI, see R. Burgada, Phosphorus and Sulfur, 13, 85 (1982).

The reaction of a compound XII with a compound XVII takes place, as a rule, without a solvent at temperatures between 50° C. and 180° C., preferably at 150° C.

as a rule, one carries out the reaction of a compound of the formula XIX with a compound of the formula XX in an inert solvent, such as tetrahydrofuran, with use of a base, such as lithium diisopropylamide, and at a temperature of −78° C. (M. P. Cooke, Tetrahedron Lett., 22, 381 (1981)).

One usually carries out the condensation of a carboxylic acid ester of the general formula IX with an aldehyde of the formula XXI in a solvent, such as methanol, ethanol, tetrahydrofuran, diethyl ether or dimethylformamide, preferably in methanol or tetrahydrofuran, in the presence of a basic condensation agent, such as sodium methylate or ethylate, potassium tert.-butylate, sodium hydride or lithium diisopropylamide, preferably sodium methylate, potassium tert.-butylate or lithium diisopropylamide, and at temperature between −78° C. and 60° C., preferably between −78° C. and room temperature.

For the allylic bromination of 2-methylfumaric or malic acid and their derivatives see J. Org. Chem. 34, 1228 (1969). As a rule, one carries at the oxidation of a compound of the general formula IX to give a compound of the general formula X in a solvent, such as tetrahydrofuran, by addition of a base, such as lithium diisopropylamide or lithium N-isopropyl-N-cyclohexylamide, with the use of an oxidation agent, such as an oxaziridine derivative, molybdenum peroxide or atmospheric oxygen, and at temperatures between −78° C. and room temperature, preferably at 50° C. (C. Tamm, Tetrahedron Lett., 26, 203 (1985); F. A. Davis, J. Org. Chem. 51, 2402 (1986); C. Winotai, Synth. Commun. 18, 2141 (1988)).

The free phosphonic acid group in compounds of the general formula I can be converted by heating with orthoformic acid trialkyl esters into the corresponding dialkyl esters. The hydrolysis of a phosphonic acid ester group in compounds of the general formula I to the corresponding free phosphonic acid group takes place, as a rule, without solvents or in an inert solvent, such as methylene chloride, by means of a trimethylsilyl halide, such as trimethylsilyl bromide or iodide, and at a temperature between −50° C. and room temperature, preferably at 0° C.

The esterification of the free carboxylic acid groups in compounds of the general formula I takes place according to processes known from the literature by heating of a compound of the general formula I, in which $R^3$ and/or $R^4$ signifies hydrogen, with an alcohol contained in the carboxylic acid ester to be prepared, with addition of an acidic catalyst, such as hydrochloric acid, sulphuric acid or p-toluenesulphonic acid, preferably sulphuric acid. One carries out the saponification of a carboxylic acid ester group in compounds of the general formula I according to conventional processes in that one treats a carboxylic acid ester of the general formula I in water or in mixtures or ethanol, preferably in a water/tetrahydrofuran mixture, with a hydroxide, such as sodium, potassium or lithium hydroxide, preferably sodium or lithium hydroxide, and at temperatures between room temperature and 80° C., preferably at room temperature.

The protective group of a primary or secondary amino group in compounds of the general formula I can be removed in that, according to conventional processes, one treats a compound of the general formula I, in which R signifies an acylamino or phthaloylimido group, with aqueous mineral acids or bases, such as hydrochloric acid or sulphuric acid or caustic soda or caustic potash solution, or reacts it with hydrazine or hyroxylamine.

Furthermore, phosphonic and carboxylic acid ester groups in compounds of the general formula I can be saponified by boiling with hydrochloric or hydrobromic acid. If benzyl esters are present in the compounds of the general formula I, then they can be converted hydrogenolytically into the corresponding free phosphonic or carboxylic acids.

As pharmacologically acceptable salts, there are, above all, used mono- or dialkali metal or ammonium salts which one prepares in the usual way, e.g. by titration of the compounds with inorganic or organic bases, such as e.g. sodium or potassium hydrogen carbonate, caustic soda solution, caustic potash solution, aqueous ammonia or amines, such as e.g. trimethyl- or triethylamine.

As a rule, the salts are purified by reprecipitation from water/acetone.

The new substances of the formula I according to the invention and their salts can be administered enterally or parenterally in liquid or solid form. All conventional forms of administration hereby come into question, for example tablets, capsules, dragees, syrups, solutions, suspension etc. As injection medium, water is preferably used which contains the additives usual in the case of injection solutions, such as stabilising agents, solubilising agents and buffers.

Such additives are e.g. tartrate and citrate buffers, ethanol, complex formers (such as ethylenediamine-tetraacetic acid and its non-toxic salts), high molecular polymers (such as liquid poly;ethylene oxide) for viscosity regulation. Liquid carrier materials for injection solutions must be sterile and are preferably filled into ampoules. Solid carrier materials are e.g. starch, lactose, mannitol, methyl cellulose, talc, highly dispersed silicic acids, high molecular fatty acids (such as stearic acid), gelatine, agar-agar, calcium phosphate, magnesium stearate, animal and vegetable fats, solid high molecular polymers (such as polyethylene glycols); compositions suitable for oral administration can, if desired, contain flavouring and sweetening materials.

The dosaging can depend upon various factors, such as manner of administration, species, age and/or individual state of health. The doses to be administered daily lie at about 10–1000 mg/human, preferably 100–500 mg/human and can be taken all at once or divided up several times.

Preferred in the meaning of the present invention are, apart from the compounds mentioned in the Examples and compounds derivable by combination of all of the meanings of the substituents mentioned in the claims, the following succinic acid derivatives, as well as their sodium and potassium salts, methyl, ethyl or bencyl esters:

a) 3-amino-2-phosphonosuccinic acid; m.p. 220° C. (decomp.)
b) 3-dimethylamino2-phosphonosuccinic acid
c) 3-(N-methyl-N-propylamino)-2-phosphonosuccinic acid
d) 3-(1-pyrrolidino)-2-phosphonosuccinic acid
e) 3-(imidazol-1-yl)-2-phosphonosuccinic acid
f) 3-aminomethyl-2-phosphonosuccinic acid; m.p. 103° C. (decomp.)
g) 3-dimethylaminomethyl-2-phosphonosuccinic acid; m.p. 112° C. (decomp.)
h) 3-(N-methyl-N-pentylamino)-methyl-2-phosphonosuccinic acid; m.p. 110° C.
i) 3-(2-dimethylaminoethyl)-2-phosphonosuccinic acid
j) 3-{2-(N-methyl-N-propylamino)-ethyl}-2-phosphonosuccinic acid
k) 2-phosphono-3-{2-(pyrrolidin-1-yl)-ethyl}-succinic acid
l) 3-{2-(imidazol-1-yl)-ethyl}-2-phosphonosuccinic acid
m) 3-(3-aminopropyl)-2-phosphonosuccinic acid; m.p. 121° C. (decomp.)
n) 2-phosphono-3-{3-(pyrrolidin-1-yl)-succinic acid
o) 3-(4-aminobutyl)-2-phosphonosuccinic acid; m.p. 135° C. (decomp.)
p) 2-phosphono-3-{4-(pyrrolidin-1-yl)-butyl}-succinic acid
q) 3-(5-aminopentyl)-2-phosphonosuccinic acid
r) 2-phosphono-3-{5-(pyrrolidin-1-yl)-pentyl}-succinic acid
s) 3-{5-(imidazol-1-yl)-pentyl}-2-phosphonosuccinic acid
t) 3-(6-aminohexyl)-2-phosphonosuccinic acid
u) 2-phosphono-3-{6-(pyrrolidin-1-yl)-hexyl}-succinic acid
v) 3-{6-(imidazol-1-yl)-hexyl}-2-phosphonosuccinic acid
w) 2-phosphono-3-(pyrid-2-yl)-succinic acid
x) 2-phosphono-3-(pyrid-3-yl)-succinic acid
y) 2-phosphono-3-(pyrid-4-yl)-succinic acid
z) 3-(imidazol-2-yl)-2-phosphonosuccinic acid
aa) 3-(imidazol-4-yl)-2-phosphonosuccinic acid
ab) 2-phosphono-3-(pyrrolidin-2-yl)-succinic acid
ac) 2-phosphono-3-(pyrrolidin-3-yl)-succinic acid
ad) 2-phosphono-3-(pyrid-2-ylmethyl)-succinic acid
ae) 2-phosphono-3-(pyrid-4-ylmethyl)-succinic acid
af) 2-phosphono-3-(pyrid-4-ylmethyl)-succinic acid
ag) 3-(imidazol-2-ylmethyl)-2-phosphonosuccinic acid
ah) 3-(imidazol-4-ylmethyl)-2-phosphonosuccinic acid
ai) 2-phosphono-3-(pyrrolidin-2-ylmethyl)-succinic acid
aj) 2-phosphono-3-(pyrrolidin-3-ylmethyl)-succinic acid
ak) 2-phosphono-3-{2-(pyrid-2-yl)-ethyl}-succinic acid
al) 2-phosphono-3-{2-(pyrid-3-yl)-ethyl}-succinic acid
am) 2-phosphono-3-{2-(pyrid-4-yl)-ethyl}-succinic acid
an) 3-{2-imidazol-2-yl)-ethyl}-2-phosphonosuccinic acid
ao) 3-{2-(imidazol-4-yl)-ethyl}-2-phosphonosuccinic acid
ap) 2-phosphono-3-{2-(pyrrolidin-2-yl)-ethyl}-succinic acid
ar) 3-{3-(imidazol-4-yl)-propyl}-2-phosphonosuccinic acid
as) 2-phosphono-3-{4-(pyrrolidin-2-yl)-butyl}-succinic acid
at) 3-(N-allyl-N-methylamino)-2-phosphonosuccinic acid
au) 3-(N-methyl-N-propargylamino)-2-phosphonosuccinic acid
av) 3-{4-(N-allyl-N-propargylamino)-butyl}-2-phosphonosuccinic acid
ax) 3-{4-(n-ethyl-N-isobutylamino)-butyl}-2-phosphonosuccinic acid
ay) 3-(azepin-1-ylmethyl)-2-phosphonosuccinic acid
az) 2-phosphono-3-{1-(pyrrolidin-1-yl)ethyl}-succinic acid
ba) 2-phosphono-3-{2-(pyrid-2-yl)-propyl}-succinic acid
bb) 2-phosphono-3-{1-methyl-1-(pyrid-3yl)-ethyl}-succinic acid
bc) 3-{3-(imidazol-1-yl)-2-methylpropyl}-2-phosphonosuccinic acid
bd) 3-(3-aminobutyl)-2-phosphonosuccinic acid
be) 3-{1,1-dimethyl-3-(N-methyl-N-pentylamino)-propyl}-2-phosphonosuccinic acid bf) 3-{3-(imidazol-4-yl)-2,3-dimethylpropyl}-2-phosphonosuccinic acid bg) 3-(2,2-dimethyl-3-dimethylaminopropyl)-2-phosphonosuccinic acid bh) 3-{2-methyl-4-(pyrrolidin-2-yl)-butyl}-2-phosphonosuccinic acid bi) 3-{2,3-dimethyl-4-(pyrrolidin-2-yl)-butyl}-2-phosphonosuccinic acid bj) 3-(5-amino-2-methylpentyl)-2-phosphonosuccinic acid bk) 2-phosphono-3-{4-(pyrid-2-yl)-but-2-enyl}-succinic acid bl) 2-phosphono-3-{4-pyrid-4-yl)-but-2-ynyl}-succinic acid The following Examples show some of the process variants which can be used for the synthesis of the compounds according to the invention. However, they do not represent a limitation of the subject matter of the invention. The structure of the compounds was verified by $^1$H-, $^{31}$P- and possibly by $^{13}$C-NMR spectroscopy. The purity of the compounds was determined by means of C, H, N, P, possibly Na analysis, as well as thin layer chromatographically or by thin layer electrophoresis (cellulose, oxalate buffer of pH=4.0).

EXAMPLE 1

2-Diethylphosphono-3-methoxycarbonyl-5-phthaloylimidovaleric acid ethyl ester

To 240 mg (10 mmol) sodium hydride in 10 ml absolute toluene one adds dropwise, with cooling, 2.24 g (10 mmol) phosphonoacetic acid triethyl ester. After ending of the evolution of hydrogen, one adds dropwise a solution of 3.26 g (10 mmol) 2-bromo-4-phthaloylimidobutyric acid methyl ester (Hoppe-Seyler Z. Physiol. Chem. 1967, 160) in 70 ml absolute toluene and allows to stir for 24 hours at room temperature. The solution is neutralised with about 1 ml ethereal hydrochloric acid, evaporated on a rotary evaporator and the remaining oil purified over 200 g of silica gel (elution agent: acetone/toluene 1:1 v/v). One obtains 2.8 g=60% of a colourless oil, the structure of which was verified by NMR spectroscopy.

EXAMPLE 2

3-(2-Aminoethyl)-2-phosphonosuccinic acid 1.5 g (3.2 mmol) of the tetraester described in Example 1 are heated under reflux for 8 hours in 40 ml 6N hydrochloric acid. The solution is concentrated to about 10 ml, the resultant precipitate filtered off with suction, the filtrate completely evaporated, the residue stirred with 3 ml of water, filtered off with suction and the filtrate again evaporated. One obtains a brownish oil which is dissolved in 2 ml of water and passed over 25 g of ion exchanger (Amberlite IR 120; H$^+$ form). The column is eluted with water and the fractions with the desired substance evaporated. One obtains 0.34 g=40% of a white, amorphous powder with the m.p.: 127°–130° C. with decomposition.

EXAMPLE 3

2-Diethylphosphono-3-ethoxycarbonyl-7-(imidazol-1-yl)-heptane-carboxylic acid ethyl ester To 48 g (2 mmol) sodium hydride in 2 ml absolute toluene one adds dropwise 552 mg (4 mmol) diethyl phosphite and, after a further 5 minutes, a solution of 588 mg (2 mmol) 4-(imidazol-1-yl)-butylfumaric acid diethyl ester in 4 ml absolute toluene. After 20 hours, one neutralises with ethereal hydrochloric acids, strips off the solvent and purifies the oily residue over 200 g of silica gel (elution agent: acetone/toluene 1:1 v/v). One obtains 380 mg=44% of a yellowish oil.

One obtains the 4-(imidazol-1-yl)-butylfumaric acid diethyl ester used as starting material in the following way:

To 72 mg (3 mmol) sodium hydride in 3 ml absolute dimethylformamide one adds 204 mg (3 mmol) imidazole. After 15 minutes, one adds to the clear yellowish solution 921 mg (3 mmol) (4-bromobutyl)-fumaric acid diethyl ester (Tetrahedron Letters, 22, 381 (1981)). One allows to stir overnight, neutralises with ethereal hydrochloric acid, evaporates and purifies the remaining oil over 150 g of silica gel (elution agent: acetone/toluene 1:1 v/v). One obtains 750 mg=41% of the desired substance as oil.

EXAMPLE 4

3-{4-(Imidazol-1-yl)-butyl}-2-phosphonosuccinic acid 432 mg (1 mmol) of the tetraester described in Example 3 are heated under reflux for 6 hours in 15 ml 6N hydrochloric acid. The solution is then evaporated, the residue dissolved in 2 ml of water and passed over 20 g of ion exchanger (Amberlite IR 120; H$^+$ form). The column is eluted with water and the fractions with the desired substance evaporated. One obtains 165 mg=52% of a white, amorphous powder with an m.p.: 161°–164° C. with decomposition.

EXAMPLE 5

2-Diethylphosphono-3-methoxycarbonyl-4-(pyrrolidin-1-yl)-butyric acid methyl ester To 1.1 g (3.74 mmol) 2-diethylphosphono-3-methoxycarbonylbut-3-enoic acid methyl ester in 10 ml absolute toluene one adds 265 mg (3174 mmol) freshly distilled pyrrolidine. One leaves the solution to stand for 24 hours at room temperature, evaporates and purifies over 100 g of silica gel (elution agent: acetone/toluene 1:4 v/v). One obtains 490 mg=38% of the desired substance as oil. The NMR spectrum confirms the structure.

One prepares the 2-diethylphosphono-3-methoxycarbonylbut-3-enoic acid methyl ester used as starting material in the following way:

To 7.19 g (30 mmol) 2-bromoethylfumaric acid dimethyl ester (J. Org. Chem., 34, 1228 (1969) one slowly adds dropwise 5.2 ml (3) mmol) triethyl phosphite. The internal temperature thereby increases to 90° C. One then heats for 1 hour to 150° C., allows to cool and purifies the oil over a silica gel column (elution agent: acetone/toluene 1:4 v/v). One obtains 4.9 g=54% of the desired compound as oil. The structure was confirmed by NMR and mass spectroscopy.

EXAMPLE 6

2-Phosphono-3-(pyrrolidin-1-ylmethyl)-succinic acid 3.65 g (10 mmol) of the tetraester described in Example 5 are heated under reflux for 6 hours in 50 ml 6N hydrochloric acid. The solution is then evaporated, the residue dissolved in 20 ml of water and purified over an ion exchanger (Amberlite IR 120; H$^+$ form). The fractions with the desired substance are evaporated and dried. One obtains 2.14 g=74% of a white powder with 0.5 mol water of crystallisation; m.p. 122°–124° C. with decomposition.

EXAMPLE 7

2-Diethylphosphono-4-(imidazol-1-yl)-3-methoxycarbonylbutyric acid methyl ester To 75 mg (3 mmol) sodium hydride in 10 ml absolute toluene one adds dropwise 205 mg (3 mmol) imidazole in 10 ml absolute tetrahydrofuran. After ending of the hydrogen evolution, one adds thereto 1.18 g (4 mmol) 2-diethylphosphono-3-methoxycarbonylbut-3-enoic acid methyl ester (see Example 5) in 20 ml absolute tetrahydrofuran and leaves to stir for 72 hours. One evaporates the mixture, adds thereto 20 ml of water, adjusts the pH=6 with 2N hydrochloric acid and extracts several times with methylene chloride. The combined organic phases are dried and evaporated. The residue is purified over 100 g of silica gel (elution agent: acetone/toluene 3:1 v/v). One obtains 610 mg=61% of the desired substance as oil. The NMR spectrum confirms the structure.

EXAMPLE 8

3-(Imidazol-1-ylmethyl)-2-phosphonosuccinic acid 1.08 g (3 mmol) of the tetraester described in Example 7 are heated under reflux for 6 hours with 30 ml 6N hydrochloric acid. One than evaporates the solution, takes up the residue in a little water, brings the solution to a pH=5 with 2N caustic soda solution, mixes it with the threefold volume of methanol and leaves to stand in a refrigerator. The precipitate formed is filtered off with suction, washed with methanol and dried. One obtains 487 mg=47% of white powder as disodium salt with 2 mol water of crystallisation; m.p. 135°–137° C. with decomposition.

Pharmacological Comparative Experiment

EXAMPLE 9

Osteoclast Assay

Material and method:

The carrying out of the experiment took place according to the method of P. Collin, H. Günther and H. Fleisch (endocrinol. 131, 1181–76, 1982) with the use of freshly isolated osteoclasts.

Special feature:

The osteoclast preparation suspended in the Medium 199 (Gibco AG, Basel, Switzerland) at pH 7.36 is treated 5 minutes before and for 25 minutes during the adhesion to wall dentine, as well as during the 24 hours assay time (in MEM Earle's), with $10^{-8}$ M of substance.

The calculation of the action (% resorption inhibition) took place in this assay according to the following formula:

| Example No. | systematic name | resorption inhibition |
|---|---|---|
| 2 | 3-(2-aminoethyl)-2-phosphonosuccinic acid | 80% |
| 6 | 2-phosphono-3-(pyrrolidin-1-ylmethyl)-succinic acid | 71% |
| 8 | 3-(imidazol-1-ylmethyl)-2-phosphonosuccinic acid | 73% |
| g) | 3-dimethylaminomethyl-2-phosphonosuccinic acid | 60% |
| a) | 3-amino-2-phosphono- | 59% |

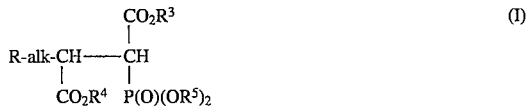

| Example No. | systematic name | resorption inhibition |
|---|---|---|
| h) | succinic acid 3-(N-methyl-N-pentyl-amino)-methyl-2-phosphono-succinic acid | 51% |

We claim:

1. A phosphonosuccinic acid derivative of the formula $$\begin{array}{c} \text{CO}_2\text{R}^3 \\ | \\ \text{R-alk-CH}\text{——}\text{CH} \\ |\quad\quad\quad | \\ \text{CO}_2\text{R}^4 \quad \text{P(O)(OR}^5)_2 \end{array} \quad (I)$$

where:

R is an amino group of the formula $-NR_1R_2$, wherein $R_1$ and $R_2$ are independently hydrogen, $C_1$–$C_6$-alkyl, $C_3$–$C_6$-alkenyl or $C_3$–$C_6$-alkynyl;

alk is a valency bond, methylene or a saturated or unsaturated, straight-chained or branched alkylene chain or 2–6 carbon atoms; and $R_3$, $R_4$ and $R_5$ are independently hydrogen;

or a pharmacologically acceptable salt or enantiomer thereof.

2. Compound of claim 1, wherein alk is methylene, ethylene, propylene, butylene, pentylene, 2-methylpropylene, hexylene or 2-butenylene.

3. The compound of claim 1 wherein the compound is 3-(2-aminoethyl)-2-phosphonosuccinic acid.

4. A pharmaceutical composition suitable for the treatment of calcium metabolism disturbances comprising a compound of the formula $$\begin{array}{c} \text{CO}_2\text{R}^3 \\ | \\ \text{R-alk-CH}\text{——}\text{CH} \\ |\quad\quad\quad | \\ \text{CO}_2\text{R}^4 \quad \text{P(O)(OR}^5)_2 \end{array} \quad (I)$$

where:

R is an amino group of the formula $-NR_1R_2$, wherein $R_1$ and $R_2$ are independently hydrogen, $C_1$–$C_6$-alkyl, $C_3$–$C_6$-alkenyl or $C_3$–$C_6$-alkynyl;

alk is a valency bond, methylene or a saturated or unsaturated, straight-chained or branched alkylene chain of 2–6 carbon atoms; and $R_3$, $R_4$ and $R_5$ are independently hydrogen;

or a pharmacologically acceptable salt or enantiomer thereof and a pharmaceutically acceptable carrier therefor.

5. A method of treatment of a calcium metabolism disturbance in a patient in need of such treatment, said method comprising administering to said patient a calcium metabolism disturbance treating amount of a compound of the formula $$\begin{array}{c} \text{CO}_2\text{R}^3 \\ | \\ \text{R-alk-CH}\text{——}\text{CH} \\ |\quad\quad\quad | \\ \text{CO}_2\text{R}^4 \quad \text{P(O)(OR}^5)_2 \end{array} \quad (I)$$

where:

R is an amino group of the formula $-NR_1R_2$, wherein $R_1$ and $R_2$ are independently hydrogen, $C_1$–$C_6$-alkyl, $C_3$–$C_6$-alkenyl or $C_3$–$C_6$-alkynyl;

alk is a valency bond, methylene or a saturated or unsaturated, straight-chained or branched alkylene chain of 2–6 carbon atoms; and $R_3$, $R_4$ and $R_5$ are independently hydrogen;

or a pharmacologically acceptable salt or enantiomer thereof.

* * * * *